US00PP25432P3

(12) United States Plant Patent
Bell

(10) Patent No.: US PP25,432 P3
(45) Date of Patent: Apr. 14, 2015

(54) ***VACCINIUM* HYBRID PLANT NAMED 'RIDLEY 1403'**

(50) Latin Name: ***Vaccinium* hybrid**
Varietal Denomination: RIDLEY 1403

(71) Applicant: Mountain Blue Orchards Pty Ltd., Lindendale, New South Wales (AU)

(72) Inventor: Ridley Bell, Lindendale (AU)

(73) Assignee: Mountain Blue Orchards Pty Ltd., Lindendale (AU)

( * ) Notice: Subject to any disclaimer, the term of this patent is extended or adjusted under 35 U.S.C. 154(b) by 141 days.

(21) Appl. No.: 13/694,258

(22) Filed: Nov. 13, 2012

(65) Prior Publication Data

US 2014/0137302 P1 May 15, 2014

(51) Int. Cl.
*A01H 5/00* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

PP20,695 P2 2/2010 Wright

*Primary Examiner* — Susan McCormick Ewoldt
(74) *Attorney, Agent, or Firm* — Davis Wright Tremaine LLP

(57) ABSTRACT

A new and distinct cultivar of *Vaccinium* hybrid plant named 'RIDLEY 1403', characterized by its combination of upright to semi-upright plant growth habit and strong plant growth vigor, evergreen foliage, very early flowering, early to medium time of ripening of fruit, very large fruit size, medium firm fruit suited to handling, attractive dark blue fruit color, flavorsome fruit with good sweetness and acidity balance and a small dry picking scar. This combination results in high quality fruit with larger size than other varieties.

4 Drawing Sheets

Latin name of genus and species of plant claimed: *Vaccinium* hybrid.

Variety denomination: 'RIDLEY 1403'.

BACKGROUND OF THE INVENTION

The present invention relates to a new and distinct perennial variety of *Vaccinium* hybrid (Southern Highbush Blueberry), which has been given the variety denomination of 'RIDLEY 1403'. Its market class is that of a fruiting plant. 'RIDLEY 1403' is intended for use as fresh fruit for shipping, customer pick and processing markets and as a home garden plant.

The new *Vaccinium* hybrid cultivar is a selection resulting from seedlings produced in a breeding programme of *Vaccinium* at Lindendale, NSW, Australia in 2006 from a controlled pollination of seed parent 'S02-25-05' (unpatented) by pollen parent 'S03-08-02' (unpatented). The new cultivar was discovered and selected as a single plant designated 'M08-14-03' within a population of one hundred plants of *Vaccinium* hybrids in 2008 in a commercial field plantation environment at Lindendale, New South Wales, Australia. Selection criteria was a combination of strong plant growth vigor, low chilling requirement, early to medium season of fruit ripening, small picking scar, strong berry firmness, high yield, very large berry size, good flavor, and sweet, crisp fruit. The selection was subsequently evaluated for over two years at commercial farms at Lindendale, New South Wales, Australia.

Asexual reproduction of the new cultivar by cutting propagation since 2008 at Lindendale, New South Wales, Australia and has demonstrated that the new cultivar reproduces true to type with all of the characteristics, as herein described, firmly fixed and retained through successive generations of such asexual propagation.

The new variety has been primarily compared to the 'C99-42' (U.S. Pat. No. 20,695). In Lindendale, New South Wales, Australia the plant growth vigour of 'RIDLEY 1403' is 'strong' whereas the plant growth vigour of 'C99-42' is 'medium to strong'. The leaf width of 'RIDLEY 1403' is 'broad' (mean 35.1 mm) whereas the leaf width of 'C99-42' is 'medium to broad' (mean 30.2 mm). The berry diameter of 'RIDLEY 1403' is 'very large (mean 24.0 mm) whereas the berry diameter of 'C99-42' is 'large' (mean 18.4 mm). The berry calyx basin diameter of 'RIDLEY 1403' is 'large' (mean 8.1 mm) whereas the berry calyx basin diameter of 'C99-42' is 'medium' (mean 6.3 mm). The berry sweetness of 'RIDLEY 1403' is rated as 'high' whereas the sweetness of 'C99-42' is 'medium'. The berry acidity of 'RIDLEY 1403' is rated as 'medium to high' whereas the acidity of 'C99-42' is 'low to medium'. This combination of vegetative and fruiting attributes results in 'RIDLEY 1403' being a desirable variety for mid season commercial production.

'RIDLEY 1403' can also be compared to the variety 'CO3-158' (unpatented). The plant growth habit of 'RIDLEY 1403' is 'upright to semi-upright' whereas the plant growth habit of 'CO3-158' is 'semi-upright'. In Lindendale, New South Wales, Australia the time of vegetative bud burst of 'RIDLEY 1403' is classified as 'early to medium' whereas the time of vegetative bud burst of 'CO3-158' is classified as 'early'. The time of beginning of flowering of 'RIDLEY 1403' is classified as 'very early' whereas the time of beginning of flowering of time of 'CO3-158' is classified as 'early to medium'. The berry shape of 'RIDLEY 1403' is round whereas the berry shape of 'CO3-158' is oblate. The berry diameter of 'RIDLEY 1403' is 'very large (mean 24.0 mm) whereas the berry diameter of 'CO3-158' is 'large' (mean 18.5 mm).The berry calyx basin diameter of 'RIDLEY 1403' is 'large' (mean 8.1 mm) whereas the berry calyx basin diameter of 'CO3-158' is 'medium to large' (mean 7.2 mm). The depth of berry calyx basin of 'RIDLEY 1403' is 'deep' whereas the depth of berry calyx basin of 'CO3-158' is 'shallow'. The berry acidity of 'RIDLEY 1403' is 'medium to high' whereas 'CO3-158' is 'medium'. See Table 1 for comparisons

SUMMARY OF THE INVENTION

The following characteristics of the new cultivar have been repeatedly observed and can be used to distinguish 'RIDLEY 1403' as a new and distinct cultivar of *Vaccinium* hybrid plant:

1. Upright to semi-upright plant growth habit
2. Very early timing of beginning of flowering
3. Early-medium timing of fruit ripening
4. Strong plant growth vigor
5. Berry diameter is very large
6. Dark blue berry color
7. Berry firmness is medium
8. Berry sweetness is medium
9. Berry acidity is medium to high
10. Picking scar is dry Plants of the new cultivar differ from plants of the seed parent 'S02-25-05' in that the berry diameter of 'RIDLEY 1403' is 'very large whereas the berry diameter of 'S02-25-05' is medium. Plant growth vigour of 'RIDLEY 1403' is 'strong' whereas the plant growth vigour of the seed parent is medium. Berry color is very dark whereas the seed parent berry color is medium dark. Plants of 'RIDLEY 1403' have an upright to semi-upright plant growth habit which is less bushy than plants of the seed parent which have a bushy semi-upright growth habit. Plants of the new cultivar differ from plants of the pollen parent 'S03-08-02' in that the berry diameter of 'RIDLEY 1403' is 'very large whereas the berry diameter of 'S03-08-02' is medium. Plants of 'RIDLEY 1403' have an upright to semi-upright plant growth habit which is less bushy than plants of the pollen parent which have a very bushy semi-upright growth habit. The berry sweetness of 'RIDLEY 1403' is rated as 'high' whereas the sweetness of the pollen parent is 'medium'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'RIDLEY 1403'.

DETAILED BOTANICAL DESCRIPTION

Figure 1:
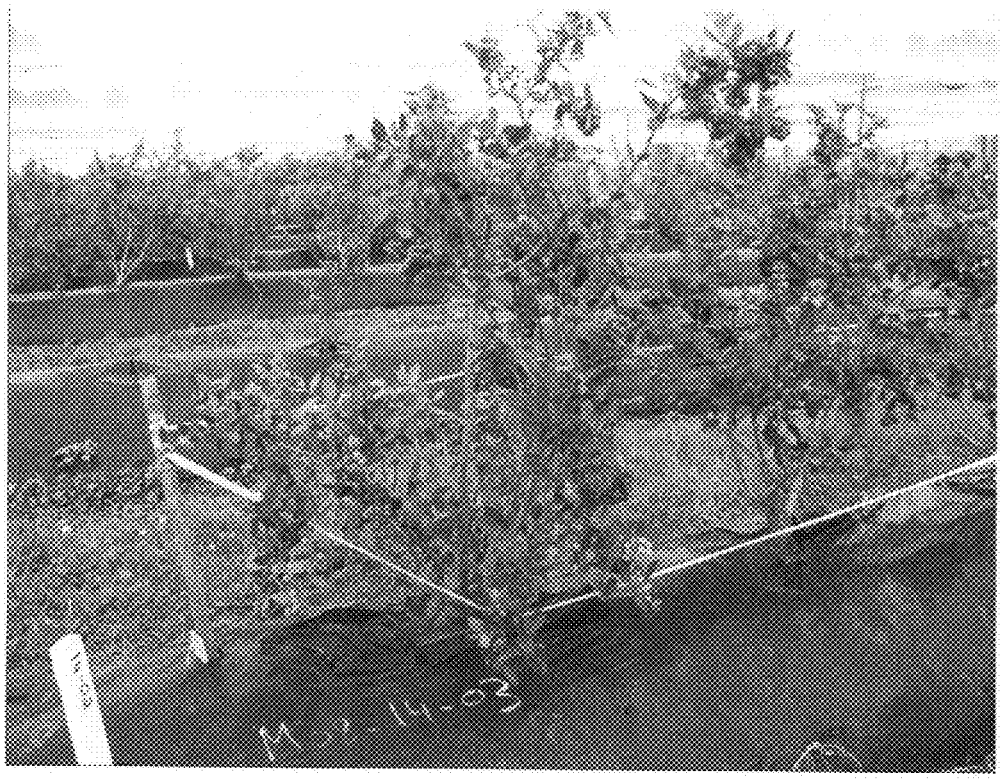
FIG. 1 illustrates a 'RIDLEY 1403' in a commercial field planting.
Figure 2:
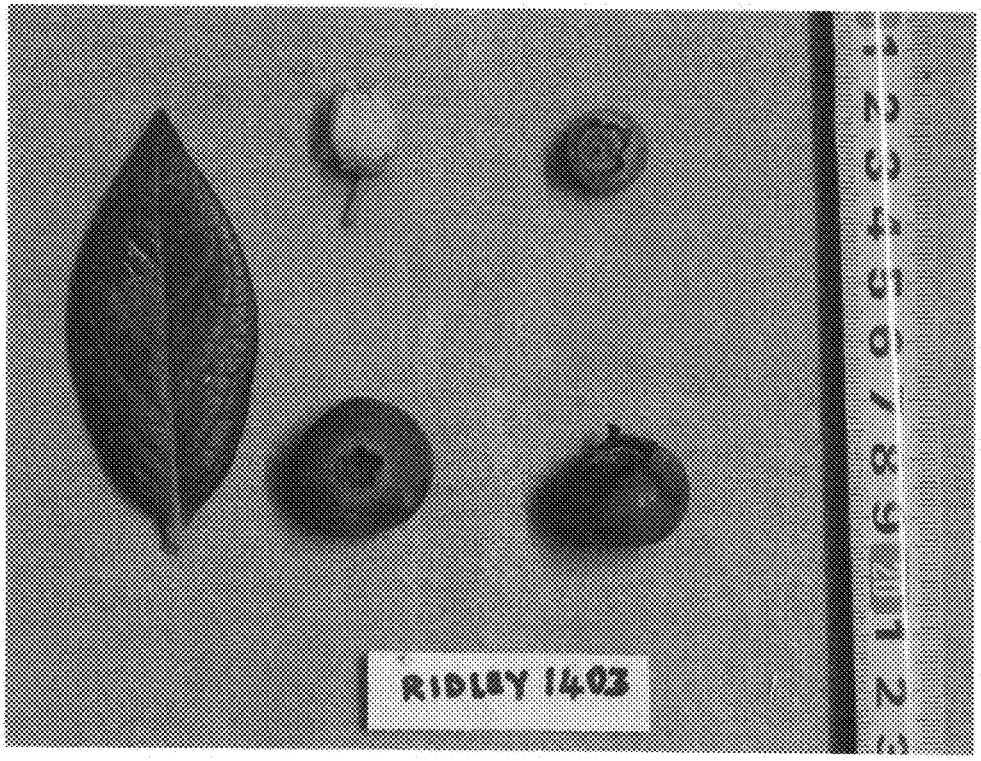
FIG. 2 illustrates a 'RIDLEY 1403' leaf, flower and berry shapes and dimensions.
Figure 3:
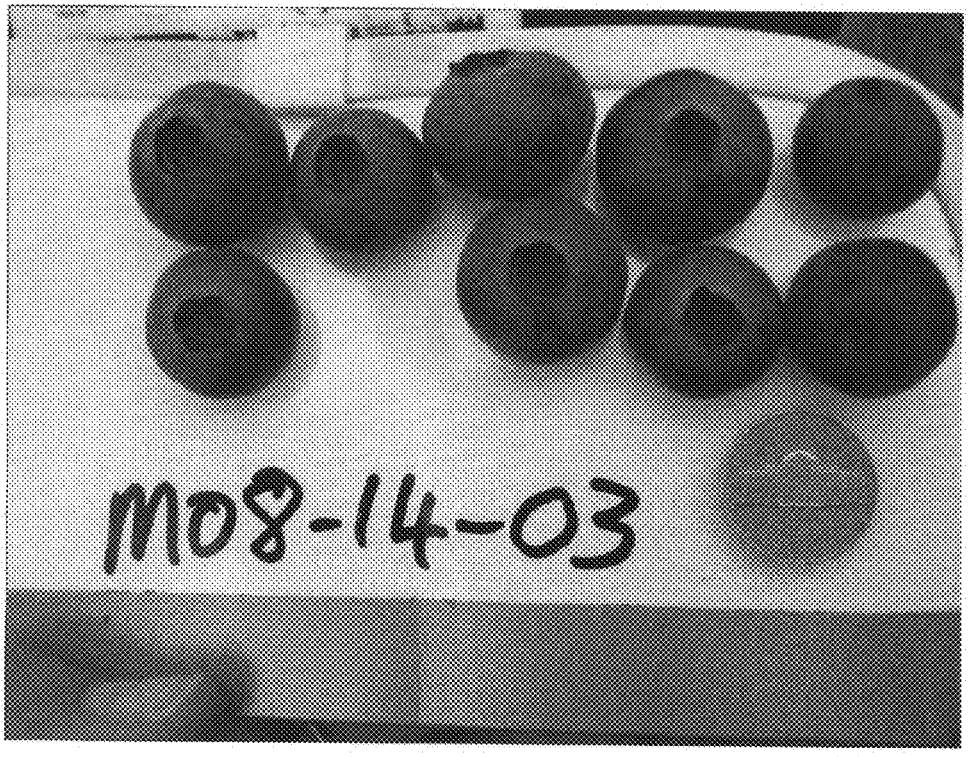
FIG. 3 illustrates 'RIDLEY 1403' berries
Figure 4:
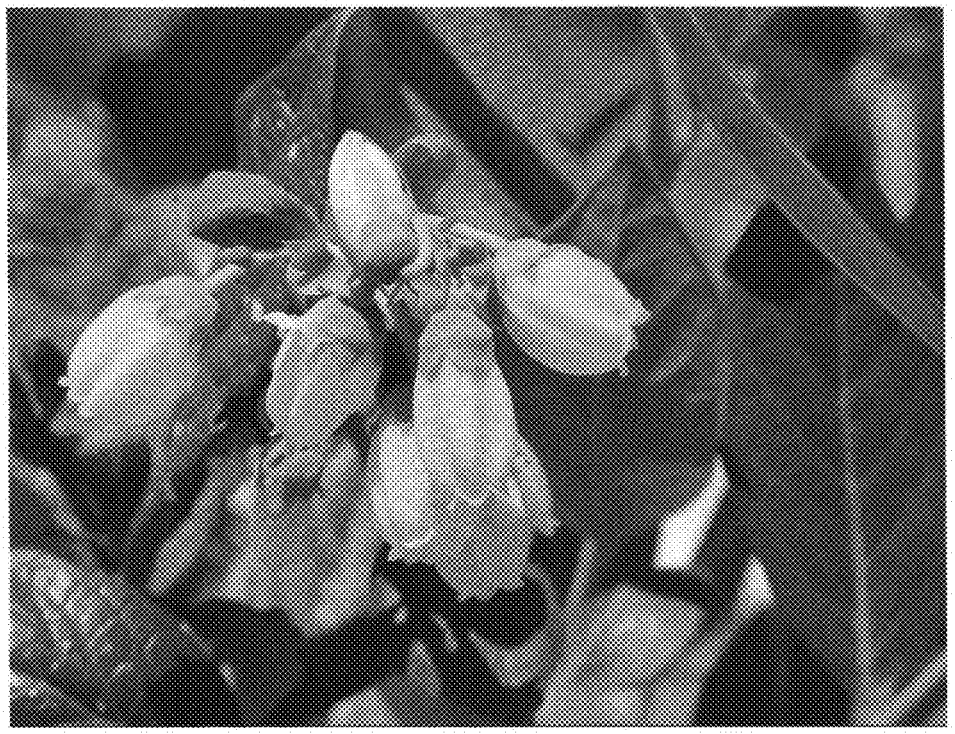
FIG. 4 illustrates a 'RIDLEY 1403' flowers

The following is a detailed botanical description of a new and distinct variety of a *Vaccinium* hybrid ornamental plant known as 'RIDLEY 1403'. Plant observations were made on plants grown in Lindendale, New South Wales, Australia. Unless indicated otherwise, the descriptions disclosed herein are based upon observations made in August 2009 of mature 'RIDLEY 1403' plants (age 4 years) grown in outdoor field plantings with day temperature ranging from 21° C. to 23° C., night temperatures ranging from 10° C. to 12° C., and light levels ranging from 6 to 8 klux. Those skilled in the art will appreciate that certain characteristics will vary with older or, conversely, younger plants. 'RIDLEY 1403' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light quality, light intensity, day length, cultural conditions and the like. Color notations are based on The Royal Horticultural Society Colour Chart, of The Royal Horticultural Society, London, 2007 edition.

Botanical classification: *Vaccinium* hybrid cultivar 'RIDLEY 1403'.

Parentage:

*Parents*.—Seed parent 'S02-25-05' (unpatented). Pollen parent 'S03-08-02' (unpatented).

Plant:

*Growth habit*.—Upright to semi-upright.
*Growth vigor*.—Is strong.
*Plant height*.—Is approximately 2.0 m.
*Plant width*.—Is approximately 1.2 m.
*Flower bud density*.—Is medium.
*Twigginess*.—Is low.
*Time of beginning of flowering*.—Is very early (begins late April to early May; peaks mid July) when grown as an evergreen in Australia.
*Time of fruit ripening*.—Is early to medium (begins mid July; peaks mid October) when grown as an evergreen in Australia.

Stem:

*Suckering tendency*.—Plants typically have 5-7 major canes per plant from a base 25 cm in diameter on 4 year old plants.
*Canes*.—Erect to semi-erect with moderate branching; color greyed green 198C; 2 year old cane diameter 11 mm, colored grayed orange 177B, some flaking of bark, current season wood diameter 3-4 mm, colored yellow green 144C. Internode length on strong, new shoots 15-20 mm.
*Fruiting wood*.—Numerous twigs to 10 cm in length.
*Surface texture of new wood*.—Smooth.

Fully developed leaf:

*Length*.—Long 70-80 mm.
*Width*.—Broad approximately 35 mm.
*Shape*.—Elliptic.
*Upper leaf surface color*.—Green 137A.
*Lower leaf surface color*.—Yellow green 147C.
*Intensity of color*.—Medium.
*Margin*.—Entire.
*Undulation of margin*.—Weak.
*Pubescence of upper side*.—Absent.
*Pubescence of lower side*.—Absent.
*Cross sectional profile*.—Flat.
*Longitudinal profile*.—Straight.
*Attitude broad*.—Acute to horizontal.
*Leaf apex*.—Acute to abruptly acute.
*Leaf base*.—Obtuse.
*Leaf venation*.—Upper and lower reticulate.

*Leaf venation upper surface color*.—Same as upper surface color green RHS 137A.

*Leaf venation lower surface color*.—Same as lower surface color yellow green RHS 147C.

*Petiole*.—Petiole length: 2.0 to 3.0 mm. Petiole diameter: 2.5 to 3.0 mm. Petiole color: yellow green RHS 147C-D, anthocyanin coloration present, approximately grayed red RHS 181 A-B, may extend into proximal half of upper and lower side midrib. Petiole texture of surface: smooth — coriaceous.

Inflorescence:

*Inflorescence diameter*.—15-20 mm.

*Inflorescence length* (*depth*).—20-30 mm.

*Length of peduncle*.—To 12 mm.

*Color of peduncle*.—Approximates to yellow green RHS 146C to 147C.

*Length of pedicel*.—Long 4-6 mm.

*Color of pedicel*.—Approximates to yellow green RHS 146C.

*Number of flowers per cluster*.—Median 8.

*Flower cluster density*.—Is medium-dense.

Flower bud:

*Size*.—Length 10 to 13 mm, diameter 6 to 7 mm.

*Shape*.—Elliptic to ovate with acute apex.

*Color*.—Corolla white RHS NN155D distally with basal anthocyanin coloration approximating RHS 181D on ridges and immature calyx lobes colored yellow green RHS 138C.

Flowers:

*Length of corolla tube*.—Medium to long (to 16 mm).

*Width of corolla tube*.—Medium to broad (to 10 mm).

*Corolla aperture diameter*.—3-5 mm.

*Color of corolla*.—White 155D.

*Anthocyanin coloration of corolla*.—Absent.

*Corolla ridges*.—Present.

*Protusion of stigma*.—Absent.

*Fragrance*.—Weak.

*Shape*.—Urceolate.

*Abundance of pollen*.—High.

*Calyx* (*with sepals*) *diameter*.—5-6 mm.

*Calyx* (*sepals*) *upper and lower surface color*.—Green 138A.

*Calyx depth* (*length*) *at flowering stage*.—3 to 4 mm.

*Sepal length at flowering stage*.—3 mm.

*Pistil*.—Pistil number: 1. Length: 9 to 11 mm. Color: yellow green RHS 138 C-D.

*Stamen*.—Stamen number: 10-15. Length: 3 mm. Color: approximately grayed orange RHS 167C-D.

Productivity: 3 to 4 kg per season from 3-4 year old plants planted at 3.0 m×0.9 m density.

Tolerance to disease: Moderate resistance to root disease (*phytophthora* spp) and good resistance to blueberry rust. Also demonstrates good resistance to Stem Blight (*Botryosphaeria dothidea*).

Resistance to pests: Is typical of the species with no documented pest problems found.

Cold hardiness: 'RIDLEY 1403' has not been grown in all environments including harsh winter environments. Cold tolerance is expected to be low.

Chilling requirement: 'RIDLEY 1403' has not been grown in all environments and is typically grown as an evergreen crop where chilling hours are not important. 'RIDLEY 1403' is classed as 'low chill', typical of Southern Highbush Blueberry varieties with an estimated chilling requirement of 250 hours (not tested).

Leafing: Plants retain leaves year round (at Lindendale, NSW Australia) and 'RIDLEY 1403' is grown commercially as an evergreen crop. New leafing occurs in mid to late August at Lindendale, NSW Australia.

Fruit:

*Unripe fruit color*.—Intensity light.

*Unripe fruit color*.—144A.

*Cluster density*.—Is medium to dense.

*Diameter*.—Is very large (mean 24 mm).

*Weight*.—Heavy (approximately 5.2 g).

*Shape*.—Round.

*Attitude of calyx*.—Erect.

*Diameter of calyx basin*.—Large (mean 8.1 mm).

*Depth of calyx basin*.—Is deep (to 3.0 mm).

*Intensity of bloom*.—Medium.

*Intensity of blue color of skin with bloom removed*.—Is dark.

*Color of skin*.—202A.

*Sweetness when ripe*.—Medium.

*Firmness when ripe*.—Medium.

*Acidity when ripe*.—Medium to high.

*Size of scar*.—Is small (1.0-1.5 mm).

*Storage*.—Quality good.

*Number of berries per cluster*.—5 to 8.

*Flesh color*.—Grayed green RHS 194A to 195A.

*Date of* 50% *maturity*.—Approximately 10$^{th}$ October at Lindendale, NSW Australia.

*Fruit development period*.—Approximately 75 days in protected cultivation at Lindendale, NSW Australia.

Seed:

*Seed color*.—Greyed orange 165B.

*Seed abundance in fruit*.—Medium.

*Seed size*.—1.6-1.8 mm long for fully developed seeds.

*Number of seeds per fruit*.—50 to 100.

TABLE 1

Comparison with other varieties (extract from Australian PBR data)

| Organ/Plant Part: Context | Ridley 1403 | C99-42 | C03-158 |
|---|---|---|---|
| Plant: growth vigour | strong | medium to strong | medium to strong |
| Plant: growth habit | upright to semi upright | upright to semi upright | semi upright |
| Leaf: length | long to very long | long to very long | long to very long |
| Leaf: width | broad | medium to broad | broad |
| Leaf: shape | elliptic | elliptic | elliptic |
| Leaf: colour of upper side | green | green | green |
| Leaf: intensity of green colour on upper side (varieties with green leaf colour only) | medium | dark | light |
| Leaf: margin | entire | entire | entire |
| Flower: size of corolla tube | medium to large | medium | medium |
| Flower: anthocyanin coloration of corolla tube | absent or very weak | weak medium | absent or very weak |
| Flower: ridges on corolla tube | present | present | present |
| Flower: protusion of stigma | absent | present | absent |
| Fruit cluster: density | medium to dense | dense | medium |
| Unripe fruit: intensity of green colour | light | light | light |
| Fruit: size | very large | large | large |
| Fruit: shape in longitudinal section | round | round | oblate |
| Fruit: attitude of sepals | erect | erect | erect |
| Fruit: diameter of calyx | large | medium | medium to |

TABLE 1-continued

| Comparison with other varieties (extract from Australian PBR data) | | | |
|---|---|---|---|
| Organ/Plant Part: Context | Ridley 1403 | C99-42 | C03-158 |
| basin | | | large |
| Fruit: depth of calyx basin | deep | deep | shallow |
| Fruit: intensity of bloom | medium | medium | medium |
| Fruit: colour of skin | dark blue | dark blue | dark blue |
| Fruit: firmness | medium | firm medium | medium to firm |
| Fruit: sweetness | medium | medium | low to medium |
| Fruit: acidity | medium to high | low to medium | medium |
| Fruit: size of scar | small | small | small |
| Fruit: average weight of ripe berry (g) | 5.2 | 2.4 | 2.8 |
| Time of: vegetative bud burst | early to medium | medium to late | early |

TABLE 1-continued

| Comparison with other varieties (extract from Australian PBR data) | | | |
|---|---|---|---|
| Organ/Plant Part: Context | Ridley 1403 | C99-42 | C03-158 |
| Time of: beginning of flowering on current years shoot | very early | early to medium | early to medium |
| Time of: beginning of fruit ripening on current years shoot | early to medium | early to medium | early to medium |

What is claimed is:

1. A new and distinct cultivar of *Vaccinium* hybrid plant named 'RIDLEY 1403', substantially as herein shown and described.

* * * * *

UNITED STATES PATENT AND TRADEMARK OFFICE

CERTIFICATE OF CORRECTION

PATENT NO. : PP25,432 P3
APPLICATION NO. : 13/694258
DATED : April 14, 2015
INVENTOR(S) : Ridley Bell It is certified that error appears in the above-identified patent and that said Letters Patent is hereby corrected as shown below:

IN THE SPECIFICATION

As part of TABLE 1 located in Col. 7, the text in the row labeled 'Fruit: depth of calyx basin' and under the column heading 'C99-42' which currently reads "deep", should be replaced with --deep to very deep--

Signed and Sealed this
Eighth Day of March, 2016

Michelle K. Lee

Michelle K. Lee
*Director of the United States Patent and Trademark Office*